United States Patent
Decitre et al.

(10) Patent No.: US 7,271,900 B2
(45) Date of Patent: Sep. 18, 2007

(54) MAGNETO-OPTICAL IMAGING METHOD AND DEVICE

(75) Inventors: Jean-Marc Decitre, Saint-Etienne (FR); Michel Lemistre, Livry-Gargan (FR); Jamal Ben Youssef, Brest (FR); Francois Lepoutre, Janvry (FR); Dominique Placko, Creteil (FR); Pierre-Yves Joubert, Paris (FR)

(73) Assignee: Centre National De La Recherche Scientifique (CNRS), Paris (FR)

( * ) Notice: Subject to any disclaimer, the term of this patent is extended or adjusted under 35 U.S.C. 154(b) by 0 days.

(21) Appl. No.: 10/562,560

(22) PCT Filed: Jun. 24, 2004

(86) PCT No.: PCT/JP2004/001602

§ 371 (c)(1),
(2), (4) Date: Dec. 27, 2005

(87) PCT Pub. No.: WO2005/001467

PCT Pub. Date: Jan. 6, 2005

(65) Prior Publication Data

US 2006/0146328 A1    Jul. 6, 2006

(30) Foreign Application Priority Data

Jun. 27, 2003    (FR)    ................... 03 07850

(51) Int. Cl.
G01J 4/00    (2006.01)
G01N 21/00    (2006.01)

(52) U.S. Cl. .................... 356/364; 356/237.2

(58) Field of Classification Search ................ 356/364, 356/369, 237.2; 250/559.05, 559.07, 559.09, 250/225; 382/149
See application file for complete search history.

(56) References Cited

U.S. PATENT DOCUMENTS

| | | | |
|---|---|---|---|
| 4,410,277 A * | 10/1983 | Yamamoto et al. | ......... 356/366 |
| 4,625,167 A | 11/1986 | Fitzpatrick | |
| 4,755,752 A | 7/1988 | Fitzpatrick | |
| 4,896,103 A | 1/1990 | Shimanuki et al. | |

(Continued)

FOREIGN PATENT DOCUMENTS

DE    40 21 359 A    1/1992

(Continued)

OTHER PUBLICATIONS

Preliminary French Search Report FR 0307850; report dated Feb. 27, 2004.

(Continued)

*Primary Examiner*—Roy M. Punnoose
(74) *Attorney, Agent, or Firm*—Miller, Matthias & Hull

(57) ABSTRACT

A quantitative magneto-optical imaging method is used to form an image of a target material. An active material is placed close to the target material and produces a Faraday rotation in a polarized light beam. The Faraday rotation of the active material is essentially proportional to the magnetization of the target material when this latter is subjected to an exciting magnetic field. Photodetector means detect the beam reflected after passing through the active material. The light from the reflected beam can then be analyzed for obtaining the amplitude and phase of an interfering magnetic field generated by a defect in the target material.

7 Claims, 3 Drawing Sheets

U.S. PATENT DOCUMENTS 5,053,704 A  10/1991  Fitzpatrick
5,446,378 A   8/1995  Reich et al.

FOREIGN PATENT DOCUMENTS

EP  0 351 171 A2   1/1990
EP  0 510 621 A2  10/1992
JP  01209356       8/1989

OTHER PUBLICATIONS

International Search Report PCT/FR2004/001602; report dated Dec. 29, 2004.

* cited by examiner

MAGNETO-OPTICAL IMAGING METHOD AND DEVICE

CROSS-REFERENCE TO RELATED APPLICATION

This is the U.S. National Phase of International Application No. PCT/FR2004/01602 filed 24 Jun. 2004, the entire disclosure of which is incorporated herein by reference.

FIELD OF THE INVENTION

The invention relates to the field of magneto-optical imaging methods and devices.

BACKGROUND OF THE INVENTION

More particularly, the invention relates to a magneto-optical imaging method comprising:
  positioning, close to a target material, a substantially plane face of a magnetic active material suitable for producing a Faraday rotation in a polarized light beam,
  generating an exciting magnetic field with angular frequency $\omega$ in the target material,
  directing a polarized incident light beam, through the active material, toward the target material,
  detecting, using photodetector means, a reflected beam corresponding to the reflection on a reflecting surface located between the active material and the target material, and
  observing the angle of Faraday rotation in the reflected beam, with respect to the incident beam, which is created in the active material by an interfering magnetic field produced by the target material.

Such methods, as well as magneto-optical apparatuses implementing such methods, are already known, in particular, by virtue of documents U.S. Pat. No. 4,625,167, U.S. Pat. No. 4,755,752, U.S. Pat. No. 5,053,704 and U.S. Pat. No. 5,446,378.

Such methods and devices are generally used, but not exclusively, to undertake nondestructive testing by eddy current. They combine the use of eddy currents and of the Faraday effect. They make it possible to detect defects, such as cracks at the feet of rivets or corrosion, that are present in a conducting target.

They find applications especially in the aeronautical and nuclear industries.

However, the known methods and devices allow only a qualitative characterization of a defect. The images obtained are binary.

An object of the invention is to provide a magneto-optical imaging method and device allowing quantitative characterization of defects.

SUMMARY OF THE INVENTION

According to an aspect of the invention, it provides a method which, in addition to the characteristics already mentioned, has the following additional characteristics:
  the Faraday rotation of the active material is substantially proportional to its magnetization when it is subjected to an interfering magnetic field, perpendicular to said face and varying in a minimum range extending between substantially −1 Oersted and substantially +1 Oersted, and that
  the value of the magnetization of the active material, under the effect of the interfering magnetic field, is determined based on the value of the angle of the Faraday rotation.

By virtue of the invention, and in particular by virtue of the use of an active material whose Faraday rotation is proportional to the field in which it is bathed, it is possible to determine, on the basis of a local luminous intensity, the value, in modulus and in phase, of the characteristic interfering magnetic field that are due to the defects in the target material. This therefore provides access, in real time, to a map of the target material accurately characterizing the defects (depth of corrosion, dimension of the cracks, etc.), especially when the method according to the invention is associated with a modeling of the means for generating of the exciting magnetic field.

The method according to the invention may furthermore comprise one and/or other of the following provisions:
  the exciting magnetic field is generated by means of an inductor energized with a variable exciter current;
  it comprises a measurement, by lock-in detection, of the variation of the phase of the interfering magnetic field with respect to that of the exciting current;
  the amplitude of the interfering magnetic field is measured based on the luminous intensity of the reflected beam;
  the incident beam is amplitude-modulated at the same frequency as that of the exciting field.

According to another aspect, the invention relates to a magneto-optical imaging device, for forming an image oaf target material, this device comprising:
  an active material, comprising a substantialy planar face, which is magnetic and suitable for producing a Faraday rotation in a polarized light beam,
  means for generating an exciting magnetic field with angular frequency $\omega$ in the active material and in the target material, when the imaging device is located close to this target material,
  a light source for directing a polarized incident light beam, through the active material, toward the target material when the imaging device is located close to this target material,
  photodetector means, for detecting a reflected beam corresponding to the reflection, after passage through the active material, of the incident beam on a reflecting surface,
  characterized in that the Faraday rotation of the active material is substantially proportional to its magnetization when it is subjected to an interfering magnetic field produced in the target material, perpendicular to said face and varying in a minimum range extending between substantially −100 Oersted and substantially +100 Oersted.

The device according to the invention may furthermore comprise one and/or other of the following provisions:
  it comprises an inductor energized with a variable exciting current, for generating the exciting magnetic field,
  it comprises modulation means of the incident beam for amplitude-modulating this latter at the same frequency as that of the exciting field; and
  it comprises calculation means for determining, based on the value of the angle of the Faraday rotation, the value of the magnetization of the active material under the effect of an interfering magnetic field produced in the active material by the target material, when the imaging device is positioned close to this target material.

DESCRIPTION OF THE EMBODIMENTS

Figure 1:
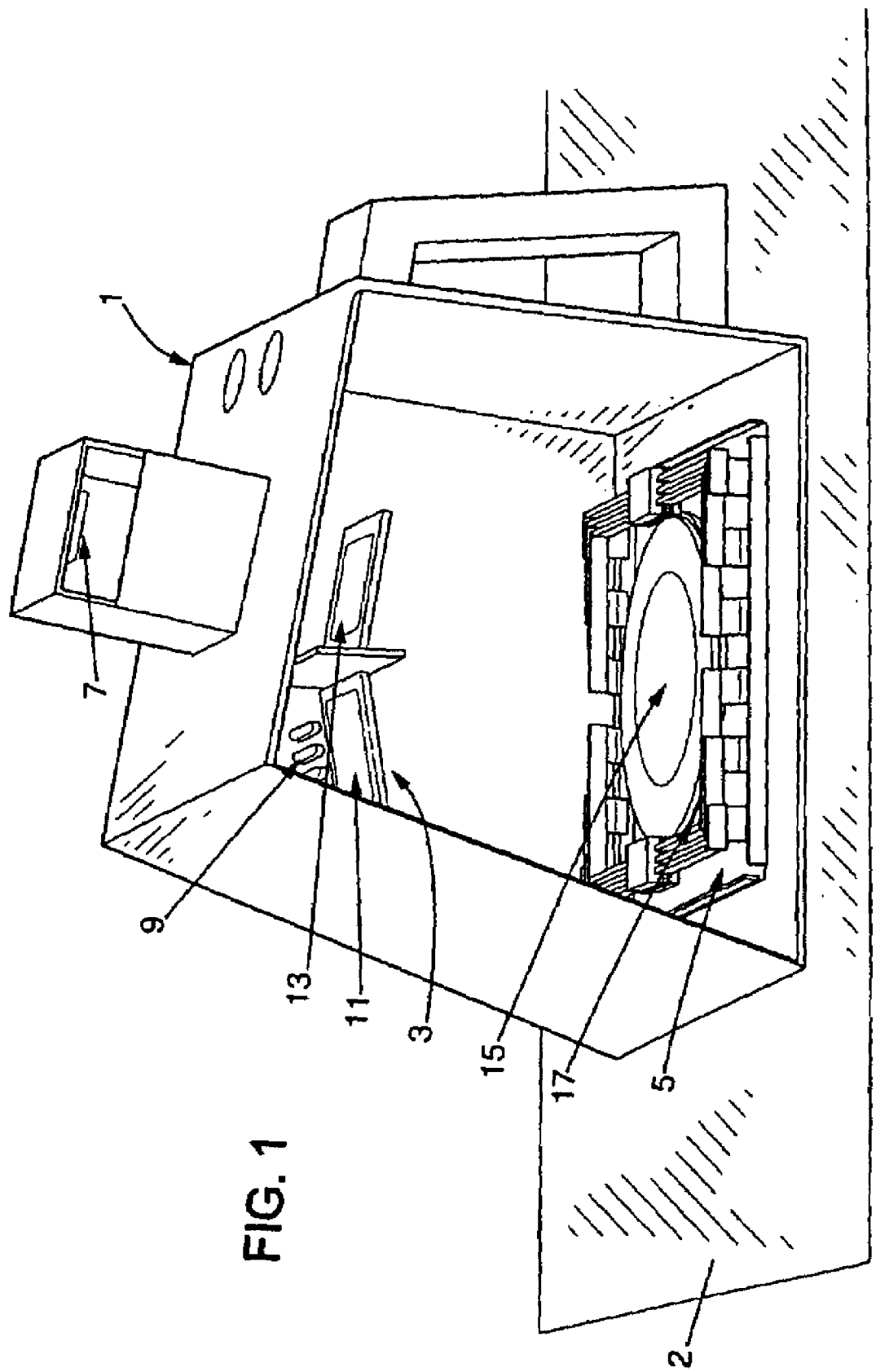
FIG. 1 diagrammatically represents in perspective a magneto-optical imaging device in accordance with the present invention.

A nonlimiting exemplary embodiment of the device according to the invention is described hereinbelow in conjunction with FIG. 1. In this example, the device comprises:
- a casing 1 suitable for being moved on the surface of a target material 2 that one wishes to analyze,
- an optical device 3,
- means 5 for generating an exciting magnetic field,
- photodetector means 7.

More precisely, the optical device 3 comprises a light source 9, a polarizer 11 and an analyzer 13. The polarizer 11 and the analyzer 13 are of a type known to the person skilled in the art.

The light source 9 is for example constituted by a light-emitting diode. Diodes of high luminosity are available on the market for varied wavelengths. A red diode 10 mm in diameter and of high luminosity (reference TLRH190P from TOSHIBA Company) will be chosen for example.

Figure 2:
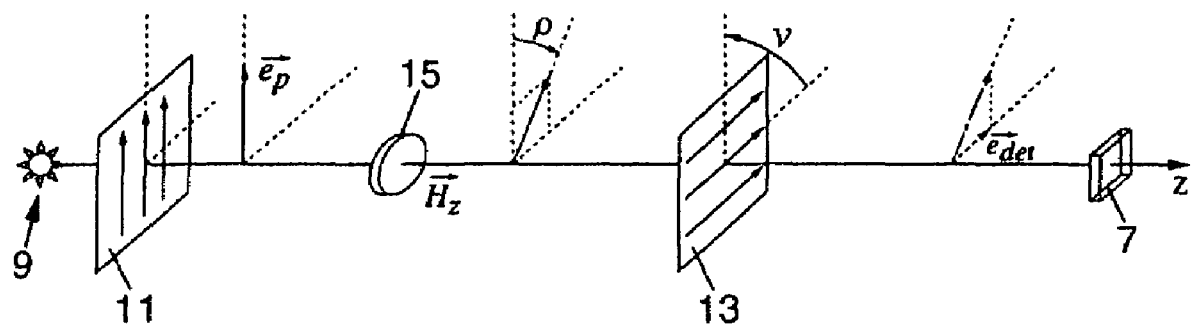
FIG. 2 diagrammatically represents the principle of magneto-optical modulation of the device represented in FIG. 1.

An optically active material 15 is interposed between the polarizer 11 and the analyzer 13, in the optical path. This polarizer/active material/analyzer assembly constitutes a magneto-optical light modulator. The principle of this magneto-optical modulator is illustrated by FIG. 2. The polarizer 11 and the analyzer 13 are crossed with an angle ν. This angle ν is advantageously chosen between 45 and 90 degrees. The polarization plane rotates under the effect of the Faraday rotation by an angle ρ.

The optically active material 15 is for example a ferrimagnetic garnet having a linear, soft magnetization cycle with little hysteresis. It is for example a $(GdPrBiTm)_3(AlFe)_5O_{12}$ compound deposited as a film 5.9 μm thick, by liquid phase epitaxy at 768° C., on an SGGG [$(GdCa)_3(GaMgZr)_5O_{12}$] substrate one inch in diameter.

In this type of garnet, the direction of easy magnetization is normal to the plane of the film.

In this type of compound, the $Bi^{3+}$ and $Pr^{3+}$ ions make it possible to obtain a strong Faraday rotation. Furthermore, they are compatible with the use of wavelengths corresponding to colors close to red. Advantageously, the magnetic domains of this type of garnet are of small dimensions compared with the size of the pixels of the photodetector means 7, thereby making it possible to average the contributions from domains with magnetization direction that are opposite.

Figure 3:
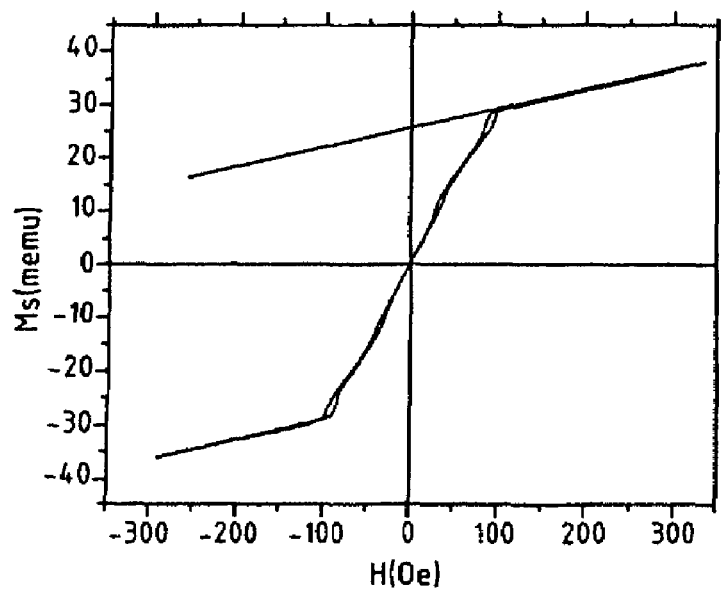
FIG. 3 represents the magnetization cycle of the active material entering into the constitution of the device represented in FIG. 1.

As represented in FIG. 3, the magnetization curve for such a garnet exhibits a substantially linear part between −100 Oersteds and +100 Oersteds approximately. Finally, it may be noted on this curve that the hysteresis is negligible and that, very advantageously, the slope, in the linear part, is greater than 1 degree/$Am^{-1}$.

One of the faces of the film of active material 15 is covered with a fine coating of aluminum acting as a mirror and thus ensuring near-total reflection of the light rays originating from the light source 9.

The optically active material 15 is immersed in a sinusoidal magnetic field of frequency f=ω/2π, created by the magnetic field generating means 5. The frequency f is for example 100 kHz.

The magnetic field generating means 5 are for example constituted by an inductive plate 17 suitable for inducing eddy currents in the target 2 (see FIG. 1). This inductive plate 17 is energized with a sinusoidal current I having a root mean square value of 120 A and a frequency f of 100 kHz. This inductive plate 17 is made of copper. It is substantially 350 μm thick and 8 centimeters by 8 centimeters square approximately. The magnetic field produced by the inductive plate is approximately 1 kA/m. The inductive plate 17 is parallel to the film of active material 15. In response to the exciting field produced by the inductive plate 17, in the presence of a defect in the target material, an interfering field $H_0$ is observed normal to the surface scanned with the face of the casing 1 parallel to the inductive plate 17.

The photodetector means 7 are advantageously constituted by a matrix, rather than by a single sensor associated with a mechanical scanning device. An analog CCD camera associated with a video acquisition card appears to be appropriate. It may be for example the XC-75CE model from SONY Company. It has indeed the following advantages:
- sufficient spatial resolution (which may even make it possible to average the values of neighboring pixels so as to minimize noise),
- simplicity of implementation and ease of matrix processing of the data based on a computer,
- relatively low cost, and
- short acquisition time, compared with systems involving multiplexing or requiring mechanical displacements.

Such CCD cameras allow the acquisition of an image every 25 to 30 milliseconds.

For compatibility between the sampling period of this CCD camera and the frequency f of excitation of the active material, the luminous intensity of the light source 9 is modulated by stroboscopy, by energizing the light source 9 with voltage pulses. In a homodyne version of the device according to the invention, the voltage pulses have a frequency identical to those of the sinusoidal current I and are with constant n2π/N out of phase (where n∈[0,N-1]).

Hence, through techniques of digital lock-in detection, it is possible to deduce the amplitude $H_0$ and the phase of the interfering magnetic field, with respect to the reference constituted by the sinusoidal current I energizing the inductive plate 17.

Indeed, if the magnetization M, of the active material, is proportional to the interfering magnetic field $H_0$, we have a Faraday rotation of the form:

$$\rho(H) = kH_0 \sin(\omega t)$$

The luminous intensity detected by the CCD camera is then proportional to $\cos^2(\nu + \rho(H))$ and, after simplification for small values of ρ, we obtain a luminous intensity proportional to $(1 + \cos 2\nu)/2 - kH_0 \sin 2\nu \sin(\omega t)$ It is thus possible to get back to the amplitude $H_0$ of the interfering field related to the defect to be characterized.

Figure 4:
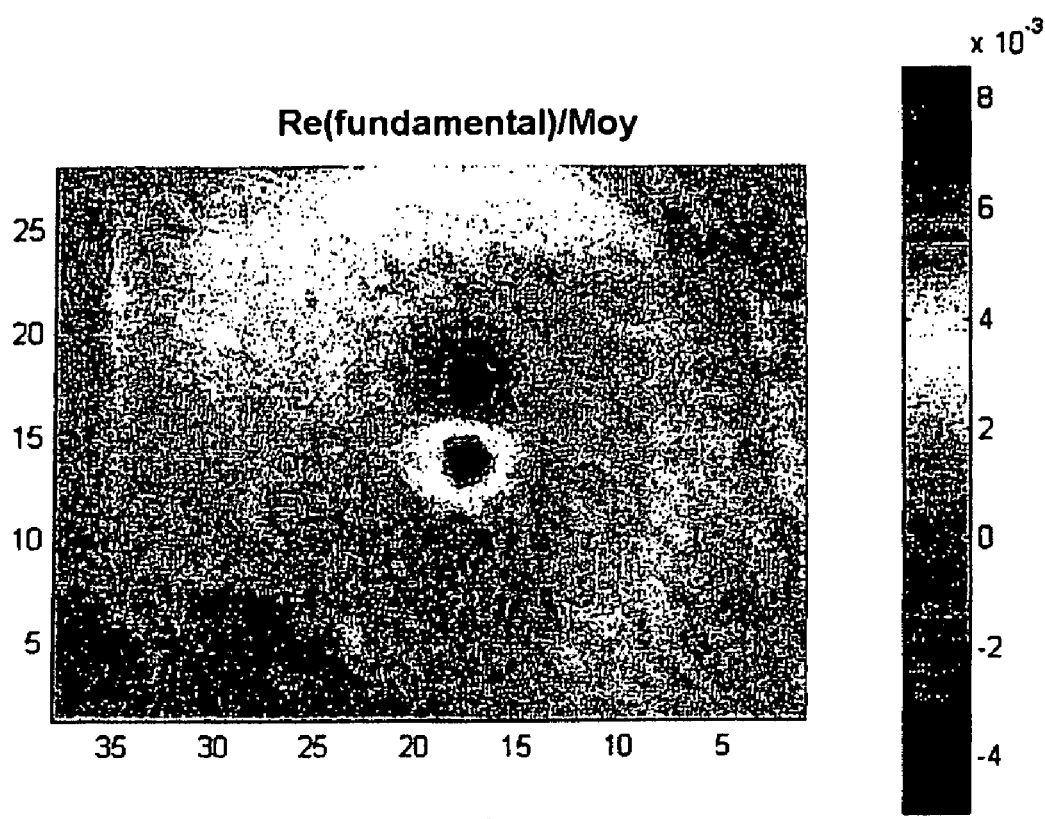
FIG. 4 represents an image of the real part of the component of the interfering magnetic field, divided by the mean luminous intensity, this image having been obtained with a device of the type of that represented in FIG. 1.
Figure 5:
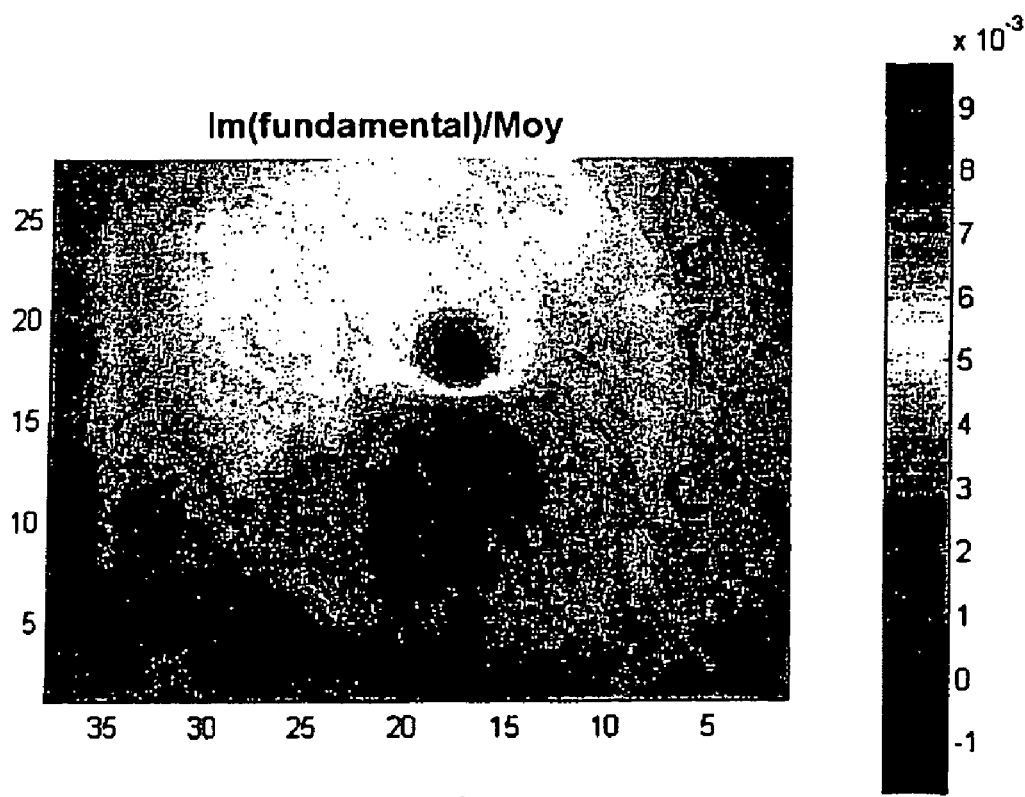
FIG. 5 represents an image of the complex part of the interfering magnetic field, divided by the mean luminous intensity, this image having been obtained with a device of the type of that represented in FIG. 1.

FIGS. 4 and 5 display results obtained for an emergent crack measuring 1 mm wide and 3 mm long, in an aluminum sheet, the inductive currents arriving perpendicularly to the largest dimension of this crack. For this measurement, I=120 A, f=100 kHz and v=80°. In FIGS. 4 and 5, the dimensions of the image are expressed in pixels. The map of the real and complex parts of the component of the interfering magnetic field are represented in FIGS. 4 and 5 respectively. These latter have been divided by the mean luminous intensity so as to circumvent any nonuniform illumination of the imaged zone of the target material, which is a few centimeters square.

By associating these results with a modeling, for example with 3D finite elements, of the means generating the exciting magnetic field 5, it is possible to accurately characterize the crack with its dimensions.

According to a variant of the method and of the device according to the invention such as were described hereinabove, a heterodyne setup is made. In this case, the frequencies of the inductive current I and of the light source are slightly different.

The invention claimed is:

1. A magneto-optical imaging method comprising:
   generating a polarized incident light beam by a light source,
   positioning, close to a tax get material, a substantially plane face of a magnetic active material suitable for producing a Faraday rotation in the polarized light beam,
   generating an exciting magnetic field of angular frequency ω in the target material,
   directing the polarized incident light beam, through the active material, toward the target material,
   observing the angle of Faraday rotation in the reflected beam, with respect to the incident beam, which is created in the active material by an interfering magnetic field produced by the target material, wherein said method also comprises:
   modulating the luminous intensity of the polarized light by the light source stroboscopy,
   lock-in detecting by photodetector means, a reflected beam corresponding to the reflection on a reflecting surface being located between the active material and the target material, and
   determining the amplitude and the phase of the interfering magnetic field, from the detected luminous intensity of the reflected beam, function of the observed angle of Faraday rotation,
   the Faraday rotation of the active material being substantially proportional to its magnetization when it is subjected to an interfering magnetic field, perpendicular to said face and varying in a minimum range extending between substantially −100 Oersted and substantially +100 Oersted.

2. The method according to claim 1, wherein the exciting magnetic field is generated by means of an inductor energized with a variable exciting current.

3. The method according to claim 2, comprising a measurement, using lock-in detection, of the variation of the phase of the interfering magnetic field with respect to that of the exciting current.

4. The method according to claim 1, wherein the incident beam is amplitude-modulated at the same frequency as that of the exciting field.

5. A magneto-optical imaging device, for forming an image of a target material, said device comprising:
   an active material, comprising a substantially planar face, which is magnetic and suitable for producing a Faraday rotation in a polarized light beam,
   means for generating an exciting magnetic field with angular frequency ω in the active material and in the target material, when the imaging device is located close to this target material,
   a light source for directing a polarized incident light beam, through the active material, toward the target material when the imaging device is positioned close to this target material, the light source generating the polarized incident light beam and modulating the intensity of the polarized light beam by stroboscopy,
   photodetector means, for detecting a reflected beam corresponding to the reflection, after passage through the active material, of the incident beam on a reflecting surface, wherein the Faraday rotation of the active material is substantially proportional to its magnetization when it is subjected to an interfering magnetic field produced by the target material, perpendicular to said face and varying in a minimum range extending between substantially −100 Oersted and substantially −100 Oersted, lock-in being detected by the photodetector means with a reflective beam corresponding to the reflection on a reflecting surface located between the active material and the target material, the amplitude and the phase of the interfering magnetic field being determined from the detected luminous intensity of the reflected beam, function of the observed angle of the Faraday rotation.

6. The device according to claim 5, comprising:
   an inductor energized with a variable exciting current, for generating the exciting magnetic field, and
   modulation means of the incident beam for amplitude-modulating the latter at the same frequency as that of the exciting field.

7. The device according to claim 6, comprising calculation means for determining, based on the value of the angle of the Faraday rotation, the value of the magnetization of the active material under the effect of an interfering magnetic field produced in the active material by the target material, when the imaging device is positioned close to this target material.

* * * * *

UNITED STATES PATENT AND TRADEMARK OFFICE
CERTIFICATE OF CORRECTION

| | | |
|---|---|---|
| PATENT NO. | : 7,271,900 B2 | Page 1 of 1 |
| APPLICATION NO. | : 10/562560 | |
| DATED | : September 18, 2007 | |
| INVENTOR(S) | : Jean-Marc Decitre et al. | |

It is certified that error appears in the above-identified patent and that said Letters Patent is hereby corrected as shown below:

\*\*On the cover page, item [86], under "PCT No.", please delete "PCT/JP2004/001602" and insert --PCT/FR2004/001602--;

\*\*In claim 1, column 5, line 26, please delete "tax get" and insert --target--; and \*\*In claim 5, column 6, line 34, please delete "-100 Oersted and substantially -100 Oersted" and insert -- -100 Oersted and substantially +100 Oersted--

Signed and Sealed this

Fifteenth Day of April, 2008

JON W. DUDAS
*Director of the United States Patent and Trademark Office*